(12) United States Patent
Chen et al.

(10) Patent No.: US 6,613,777 B1
(45) Date of Patent: Sep. 2, 2003

(54) CRF ANTAGONISTIC PYRAZOLO[4,3-B] PYRIDINES

(76) Inventors: Chen Chen, 13922 Sparren Ave., San Diego, CA (US) 92129; Keith M. Wilcoxen, 125 W. Brookes Ave., San Diego, CA (US) 92103; Charles Q. Huang, 12341 Goldfish Ct., San Diego, CA (US) 92129; Mustapha Hadduch, 3545 Arnold Ave., San Diego, CA (US) 92104; James R. McCarthy, 401 Loma Larga, Solana Beach, CA (US) 92075

( * ) Notice: Subject to any disclaimer, the term of this patent is extended or adjusted under 35 U.S.C. 154(b) by 0 days.

(21) Appl. No.: 09/623,634

(22) PCT Filed: Feb. 26, 1999

(86) PCT No.: PCT/EP99/01307

§ 371 (c)(1),
(2), (4) Date: Feb. 20, 2001

(87) PCT Pub. No.: WO99/45007

PCT Pub. Date: Sep. 10, 1999

Related U.S. Application Data

(60) Provisional application No. 60/077,311, filed on Mar. 6, 1998.

(51) Int. Cl.$^7$ .......................... A61K 31/44; A61P 25/00; C07D 471/02
(52) U.S. Cl. ....................... 514/303; 546/119
(58) Field of Search .......................... 546/119; 514/303

(56) References Cited

U.S. PATENT DOCUMENTS 4,833,136 A * 5/1989 Markwell et al. ........... 514/212

FOREIGN PATENT DOCUMENTS

| EP | 0 239 191 | 9/1987 |
|---|---|---|
| EP | 0 773 023 | 5/1997 |
| EP | 0 778 277 | 6/1997 |
| WO | WO 94/13643 | 6/1994 |
| WO | WO 94/13676 | 6/1994 |
| WO | WO 94/13677 | 6/1994 |
| WO | WO 95/10506 | 4/1995 |
| WO | WO 95/33750 | 12/1995 |
| WO | WO 97/29109 | 8/1997 |
| WO | WO 98/03510 | 1/1998 |
| WO | WO 98/29413 | 7/1998 |

OTHER PUBLICATIONS

Chorvat, R.J., et al., "Synthesis, Corticotropin–releasing Factor Receptor Binding Affinity, and Pharmacokinetic Properties of Triazolo–, Imidazo—and Pyrrolopyrimidines and —pyridines", *J. Med. Chem.*, vol. 42, No. 5, Mar. 1999 pp. 833–848.

Christos, T.E., et al., "Corticotropin–releasing factor antagonists", *Exp. Opin. Ther. Patents*, vol. 8, No. 2, Feb./ 1998, pp. 143–152.

Owens, M. J., et al. "Physiology and Pharmacology of Corticotropin–releasing Factor", *Pharmacological Reviews*, vol. 43, No. 4, Jan. 1991.

Wustrow D.J., et al., "Pyrazolo '1,5–β–pyrimidine CRF–1 receptor antagonists", *Bioorganic and Medicinal Chemistry Letters*, vol. 8, No. 16, Aug. 1998, pp. 2067–2070.

* cited by examiner

*Primary Examiner*—Brenda Coleman
(74) *Attorney, Agent, or Firm*—Scully, Scott, Murphy & Presser

(57) ABSTRACT

This invention concerns compounds of formula

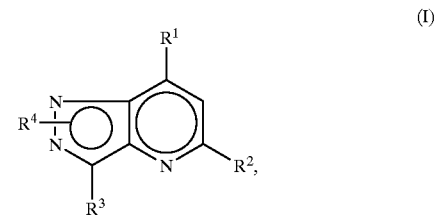

(I)

including the stereoisomers and the pharmaceutically acceptable acid addition salt forms thereof, wherein $R^1$ is $C_{1-6}$alkyl, $NR^5R^6$, $OR^6$ or $SR^6$; $R^2$ is $C_{1-6}$alkyl, $C_{1-6}$alkyloxy, or $C_{1-6}$alkylthio; $R^3$ is $Ar^1$ or $Het^1$; $R^4$ is hydrogen or $C_{1-6}$alkyl; $R^5$ is hydrogen, $C_{1-8}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl, mono- or di($C_{1-6}$alkyl)amino-$C_{1-6}$alkyl or $C_{1-6}$alkyloxy$C_{1-6}$alkyl; $R^6$ is $C_{1-8}$alkyl, mono- or di($C_{3-6}$cycloalkyl)methyl, $Ar^2C_{1-6}$alkyl, $Ar^2$oxy$C_{1-6}$alkyl, $C_{1-6}$alkyloxy$C_{1-6}$alkyl, hydroxy$C_{1-6}$alkyl, $C_{3-6}$alkenyl, thienylmethyl, furanylmethyl, tetrahydrofuranylmethyl, $C_{1-6}$alkylthio$C_{1-6}$alkyl, mono- or di($C_{1-6}$alkyl)amino$C_{1-6}$alkyl, di($C_{1-6}$alkyl)amino, or $C_{1-6}$alkylcarbonyl$C_{1-6}$alkyl; or $R^5$ and $R^6$ taken together with the nitrogen atom to which they are attached may form a pyrrolidinyl, piperidinyl, homopiperidinyl, morpholinyl, or thiomorpholinyl group, optionally substituted with 1 or 2 substituents each independently selected from $C_{1-6}$alkyl or $C_{1-6}$alkyloxy$C_{1-6}$alkyl; and and $Ar^1$ and $Ar^2$ are each optionally substituted phenyl; and $Het^1$ is optionally substituted pyridinyl; having CRF receptor antagonistic properties; pharmaceutical compositions containing such compounds as active ingredients; methods of treating disorders related to hypersecretion of CRF such as depression, anxiety, substance abuse, by administering an effective amount of a compound of formula (I).

15 Claims, No Drawings

CRF ANTAGONISTIC PYRAZOLO[4,3-B] PYRIDINES

RELATED APPLICATIONS

The present application is based on PCT Application Serial No. PCT/EP99/01307, filed on Feb. 26, 1999 which is claiming priority of U.S. provisional application No. 60/077,311, filed on Mar. 6, 1998.

BACKGROUND OF THE INVENTION

This invention relates to pyrazolo[4,3-b]pyridines which possess CRF receptor antagonistic properties, to pharmaceutical compositions containing these compounds as active ingredient, and the use thereof in the treatment of endocrine, psychiatric and neurologic conditions or illnesses, including stress-related disorders in general.

The first corticotropin-releasing factor (CRF) was isolated from ovine hypothalmi and identified as a 41-amino acid peptide (Vale et al., Science 213:1394–1397, 1981). Subsequently, sequences of human and rat CRF were isolated and determined to be identical, but different from ovine CRF in 7 of the 41 amino acid residues (Rivier et al., Proc. Natl. Acad. Sci. USA 80:4851, 1983; Shibahara et al., EMBO J. 2:775, 1983). CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., Science 213:1394–1397, 1981). Briefly, CRF is believed to initiate its biological effects by binding to a plasma membrane receptor which has been found to be distributed throughout the brain (DeSouza et al., Science 221:1449–1451, 1984), pituitary (DeSouza et al., Methods Enzymol. 124:560, 1986; Wynn et al., Biochem. Biophys. Res. Comm. 110:602–608, 1983), adrenals (Udelsman et al., Nature 319:147–150, 1986) and spleen (Webster, E. L., and E. B. DeSouza, Endocrinology 122:609–617, 1988). The CRF receptor is coupled to a GTP-binding protein (Perrin et al., Endocrinology 118: 1171–1179, 1986) which mediates CRF-stimulated increase in intracellular production of cAMP (Bilezikjian, L. M., and W. W. Vale, Endocrinology 113:657–662, 1983).

In addition to its role in stimulating the production of ACTH and POMC, CRF is also believed to coordinate many of the endocrine autonomic, and behavioral responses to stress, and may be involved in the pathoplhysiology of affective disorders. Moreover, CRF is believed to be a key intermediary in communication between the immune, central nervous, endocrine and cardiovascular systems (Crofford et al., J. Clin. Invest. 90:2555–2564, 1992; Sapolsky et al., Science 238:522–524, 1987; Tilders et al., Regul. Peptides 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., Nature 297:331, 1982), persistent activation of the electroencephalogram (Ehlers et al., Brain Res. 2/8332, 1983), stimulation of the sympathoadrenomedullary pathway (Brown et al., Endocrinology 110:928, 1982), an increase of heart rate and blood pressure (Fisher et al., Endocrinology 110:2222, 1982), an increase in oxygen consumption (Brown et al., Life Sciences 30:207, 1982), alteration of gastrointestinal activity (Williams et al., Am. J. Physiol. 253:G582, 1987), suppression of food consumption (Levine et al., Neuropharmacology 22:337, 1983), modification of sexual behavior (Sirinathsinghji et al., Nature 305:232, 1983), and immune function compromise (Irwin et al., Am. J. Physiol. 255:R744, 1988). Furthermore, clinical data suggest that CRF may be hypersecreted in the brain in depression, anxiety-related disorders, and anorexia nervosa. (DeSouza, Ann. Reports in Med. Chem. 25:215–223, 1990).

Accordingly, clinical data suggest that CRF receptor antagonists may represent novel antidepressant and/or anxiolytic drugs that may be useful in the treatment of the neuropsychiatric disorders manifesting hypersecretion of CRF.

Due to the physiological significance of CRF, the development of further biologically active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

CRF receptor antagonists have been reported in for example, WO-94/13676, WO-94/13677, WO-95/33750 and WO-96/35689 which disclose pyrrolopyrimidines, pyrazolo [3,4-d]pyrimidines and substituted purines as CRF receptor antagonists. WO-98/03510, published on Jan. 29, 1998, discloses azolotriazine and pyrimidine derivatives as CRF antagonists. Also WO-97/29109, published Aug. 14, 1997, discloses CRF antagonistic pyrazolopyrimidines.

Structurally related pyrazolo[4,3-b]pyridines are also disclosed in EP-0,239,191-A, published Sep. 30, 1987, as being useful for treating inflammatory or allergic conditions.

Other structurally related compounds are disclosed in Japanese Published (Kokai) patent application No. 52-077086 having anti-inflammatory and anti-bacterial properties. Furthermore, J. Heterocycl. Chem., 8(6), pp 1035–1037 (1971) describes pyrazolopyridines having CNS antidepressant activity in mice.

The compounds of the present invention differ from the cited art-known compounds structurally, by the nature of the substituents on the pyrazolo[4,3-b]pyridine moiety, and pharmacologically by the fact that, unexpectedly, these compounds have CRF antagonistic properties.

DESCRIPTION OF THE INVENTION

This invention concerns CRF antagonistic compounds of formula (I)

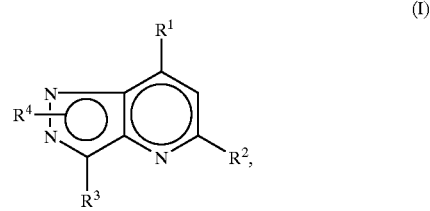

including the stereoisomers and the pharmaceutically acceptable acid addition salt forms thereof, wherein $R^1$ is $C_{1-6}$alkyl, $NR^5R^6$, $OR^6$ or $SR^6$;

$R^2$ is $C_{1-6}$alkyl, $C_{1-6}$alkyloxy, or $C_{1-6}$alkylthio;

$R^3$ is $Ar^1$ or $Het^1$;

$R^4$ is hydrogen or $C_{1-6}$alkyl;

$R^5$ is hydrogen, $C_{1-8}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl, mono- or di($C_{1-6}$alkyl)amino$C_{1-6}$alkyl or $C_{1-6}$alkyloxy$C_{1-6}$alkyl;

$R^6$ is $C_{1-8}$alkyl, mono- or di($C_{3-6}$cycloalkyl)methyl, $Ar^2C_{1-6}$alkyl, $Ar^2$oxy$C_{1-6}$alkyl, $C_{1-6}$alkyloxy$C_{1-6}$alkyl, hydroxy$C_{1-6}$alkyl, $C_{3-6}$alkenyl, thienylmethyl, furanylmethyl, tetrahydrofuranylmethyl, $C_{1-6}$alkylthio$C_{1-6}$alkyl, mono- or di($C_{1-6}$alkyl)amino$C_{1-6}$alkyl, di($C_{1-6}$alkyl)amino, or $C_{1-6}$alkylcarbonyl$C_{1-6}$alkyl;

or $R^5$ and $R^6$ taken together with the nitrogen atom to which they are attached may form a pyrrolidinyl, piperidinyl, homopiperidinyl, morpholinyl, or thiomorpholinyl group, optionally substituted with 1 or 2 substituents each independently selected from $C_{1-6}$alkyl or $C_{1-6}$alkyloxy$C_{1-6}$alkyl;

$Ar^1$ is phenyl; naphtyl; or phenyl substituted with 1, 2 or 3 substituents each independently selected from halo, $C_{1-6}$alkyl, trifluoromethyl, hydroxy, cyano, $C_{1-6}$alkyloxy, benzyl, benzyloxy, $C_{1-6}$alkylthio, nitro, amino and mono- or di($C_{1-6}$alkyl)amino;

$Het^1$ is pyridinyl; pyridinyl substituted with 1, 2 or 3 substituents each independently selected from halo, $C_{1-6}$alkyl, trifluoromethyl, hydroxy, cyano, $C_{1-6}$alkyloxy, benzyloxy, $C_{1-6}$alkylthio, nitro, amino, and mono- or di($C_{1-6}$alkyl)amino; and $Ar^2$ is phenyl; phenyl substituted with 1, 2 or 3 substituents each independently selected from halo, hydroxy, $C_{1-6}$alkyl, $C_{1-6}$alkyloxy, di($C_{1-6}$alkyl)amino$C_{1-6}$alkyl, or trifluoromethyl; or pyridinyl.

In an aspect this invention also concerns the novel compounds of formula (I), which hereinafter and in the claims will be referred to as compounds of formula (I-1) wherein $R^1$ to $R^4$ are defined hereinabove and wherein at least $R^1$ is $C_{1-6}$alkyl; $OR^6$; $SR^6$; or $NR^5R^6$ wherein $R^5$ is mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl, mono- or di($C_{1-6}$alkyl)amino$C_{1-6}$alkyl or $C_{1-6}$alkyloxy$C_{1-6}$alkyl, and $R^6$ is mono- or di($C_{3-6}$cycloalkyl)methyl, $Ar^2C_{1-6}$alkyl, $Ar^2$oxy$C_{1-6}$alkyl, hydroxy$C_{1-6}$alkyl, $C_{1-6}$alkyloxy$C_{1-6}$alkyl, $C_{1-6}$alkenyl, thienylmethyl, furanylmethyl, tetrahydrofuranylmethyl, $C_{1-6}$alkylthio$C_{1-6}$alkyl, $C_{1-6}$alkylcarbonyl$C_{1-6}$alkyl, mono- or di($C_{1-6}$alkyl)amino$C_{1-6}$alkyl, or di($C_{1-6}$alkyl)amino; or $R^5$ and $R^6$ taken together with the nitrogen atom to which they are attached may form a pyrrolidinyl, piperidinyl, or homopiperidinyl, each substituted with 1 or 2 substituents independently selected from $C_{1-6}$alkyl or $C_{1-6}$alkyloxy$C_{1-6}$alkyl; or $R^5$ and $R^6$ taken together with the nitrogen atom to which they are attached may form a morpholinyl or a thiomorpholinyl group, optionally substituted with 1 or 2 substituents independently selected from $C_{1-6}$alkyl or $C_{1-6}$alkyloxy$C_{1-6}$alkyl; or, at least $R^3$ is $Het^1$ or $Ar^1$ wherein $Ar^1$ is naphtyl; or phenyl substituted with 3 substituents each independently selected from halo, $C_{1-6}$alkyl, trifluoromethyl, hydroxy, cyano, $C_{1-6}$alkyloxy, benzyl, benzyloxy, $C_{1-6}$alkylthio, nitro, amino and mono- or di($C_{1-6}$alkyl)amino.

As used in the foregoing definitions and hereinafter, halo is generic to fluoro, chloro, bromo and iodo; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; $C_{2-4}$alkyl defines straight saturated hydrocarbon radicals having from 1 to 2 carbon atoms such as methyl and ethyl; $C_{2-4}$alkyl defines straight and branched chain saturated hydrocarbon radicals having from 2 to 4 carbon atoms such as ethyl, propyl, butyl, 1-methyletlhyl and the like; $C_{3-4}$alkyl defines straight and branched chain saturated hydrocarbon radicals having from 3 to 4 carbon atoms such as propyl, butyl, 1-methylethyl and the like; $C_{1-6}$alkyl includes $C_{1-2}$alkyl and $C_{3-4}$alkyl radicals as defined hereinbefore and the higher homologues thereof having from 5 to 6 carbon atoms such as, pentyl, the pentyl isomers, hexyl and the hexyl isomers; $C_{1-8}$alkyl includes $C_{1-6}$alkyl and the higher homologues thereof having from 7 to 8 carbon atoms such as, for example, heptyl, octyl and the like; $C_{3-6}$alkenyl defines straight and branched chain hydrocarbon radicals containing one double bond and having from 3 to 6 carbon atoms such as, for example, 2-propenyl, 3-butenyl, 2-pentenyl, 3-pentenyl, 3-methyl-2-butenyl, and the like; and where said $C_{3-6}$alkenyl is linked to a nitrogen or oxygen, the carbon atom making the link preferably is saturated. $C_{3-6}$cycloalkyl comprises cyclopropyl, cyclobutyl, cyclopentyl and cyclohexyl. Hydroxy$C_{1-6}$alkyl refers to $C_{1-6}$alkyl substituted with a hydroxy group.

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention. For instance, compounds of formula (I) wherein $R^4$ is hydrogen exist as tautomers as depicted below.

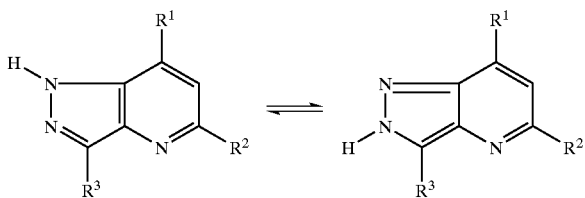

Whenever used hereinafter, the term "compounds of formula (I)" is meant to include also the pharmaceutically acceptable acid addition salts and all stereoisomeric forms.

The numbering of the bicyclic ring-system present in the compounds of formula (I) is shown below:

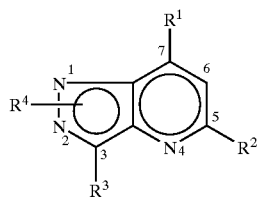

Interesting groups of compounds within the invention are those compounds of formula (I) wherein one or more of the radicals have the following meaning:

a) $R^1$ is $NR^5R^6$ wherein $R^5$ is hydrogen or $C_{1-8}$alkyl; in particular $C_{2-4}$alkyl; and $R^6$ is $C_{1-8}$alkyl or $C_{3-6}$cycloalkylmethyl; in particular $C_{2-4}$alkyl or cyclopropylmethyl;

b) $R^1$ is $OR^6$ or $SR^6$ wherein $R^6$ is $C_{1-6}$alkyl; in particular $C_{1-4}$alkyl;

c) $R^2$ is $C_{1-6}$alkyl; in particular $C_{1-2}$alkyl;

d) $R^3$ is a phenyl substituted with 1, 2 or 3 substituents each independently selected from $C_{1-6}$alkyl, $C_{1-6}$alkyloxy or halo; wherein the phenyl moiety is preferably substituted in the 3-, 4-, 6-, 2,4- or 2,4,6- positions; or $R^3$ is a pyridinyl substituted with 1, 2 or 3 substituents each independently selected from halo, amino, nitro, trifluoromethyl, mono- or di($C_{1-6}$alkyl)amino, or $C_{1-6}$alkyl; wherein the pyridinyl moiety preferably is connected via the 2- or 3-position to the remainder of the molecule; and e) $R^4$ is hydrogen or $C_{1-6}$alkyl.

Particular compounds are those compounds of formula (I) wherein $R^1$ is $NR^5R^6$ and $R^5$ is $C_{3-4}$alkyl, preferably propyl; $R^6$ is $C_{3-4}$alkyl or cyclopropylmethyl, preferably propyl; $R^2$ is methyl; $R^3$ is a phenyl substituted with 1, 2 or 3 substituents each independently selected from halo, methyl or methoxy; or $R^3$ is pyridinyl substituted with 1, 2 or 3 substituents each independently selected from halo, methyl or dimethylamino; and $R^4$ is hydrogen or methyl.

Other particular compounds are those compounds of formula (I) wherein $R^3$ is phenyl substituted on the 2- and 4-position with $C_{1-2}$alkyl or halo; in particular $R^3$ is 2,4-dichlorophenyl.

Interesting novel compounds of formula (I-1) are those compounds of formula (I-1) wherein one or more of the radicals have the following meaning:

a) $R^1$ is $NR^5R^6$ wherein $R^5$ is hydrogen or $C_{1-8}$alkyl; in particular $C_{2-4}$alkyl; and $R^6$ is $C_{1-8}$alkyl or $C_{3-6}$cycloalkylmethyl; in particular $C_{2-4}$alkyl or cyclopropylmethyl;

b) $R^1$ is $OR^6$ or $SR^6$ wherein $R^6$ is $C_{1-6}$alkyl; in particular $C_{1-4}$alkyl;

c) $R^2$ is $C_{1-6}$alkyl; in particular $C_{1-2}$alkyl;

d) $R^3$ is a phenyl substituted with 3 substituents each independently selected from $C_{1-6}$alkyl, $C_{1-6}$alkyloxy or halo; or $R^3$ is a pyridinyl substituted with 1, 2 or 3 substituents each independently selected from halo, amino, nitro, trifluoromethyl, mono- or di($C_{1-6}$alkyl)amino, or $C_{1-6}$alkyl; wherein the pyridinyl moiety preferably is connected via the 2- or 3-position to the remainder of the molecule; and e) $R^4$ is hydrogen or $C_{1-6}$alkyl.

Particular novel compounds of formula (I-1) are those compounds of formula (I-1) wherein $R^1$ is a radical of formula $NR^5R^6$ wherein $R^5$ is mono- or di($C_{3-6}$cycloalkyl)-methyl, $C_{3-6}$cycloalkyl, $C_{3-6}$alkenyl, hydroxy$C_{1-6}$alkyl, $C_{1-6}$alkylcarbonyloxy$C_{1-6}$alkyl, mono- or di($C_{1-6}$alkyl)amino$C_{1-6}$alkyl or $C_{1-6}$alkyloxy$C_{1-6}$alkyl, and $R^6$ is mono- or di($C_{3-6}$cycloalkyl)methyl, $Ar^2C_{1-6}$alkyl, $Ar^2oxyC_{1-6}$alkyl, hydroxy$C_{1-6}$alkyl, $C_{1-6}$alkyloxy$C_{1-6}$alkyl, $C_{3-6}$alkenyl, thienylmethyl, furanylmethyl, tetrahydrofuranylmethyl, $C_{1-6}$alkylthio$C_{1-6}$alkyl, $C_{1-6}$alkylcarbonyl$C_{1-6}$alkyl, mono- or di($C_{1-6}$alkyl)amino$C_{1-6}$alkyl, or di($C_{1-6}$alkyl)amino.

Other particular novel compounds of formula (I-1) are those compounds of formula (I-1) wherein $R^1$ is a radical of formula $NR^5R^6$ wherein $R^5$ and $R^6$ taken together with the nitrogen atom to which they are attached may form a pyrrolidinyl, piperidinyl, or homopiperidinyl, each substituted with 1 or 2 substituents independently selected from $C_{1-6}$alkyl or $C_{1-6}$alkyloxy$C_{1-6}$alkyl; or $R^5$ and $R^6$ taken together with the nitrogen atom to which they are attached may form a morpholinyl or a thiomorpholinyl group, optionally substituted with 1 or 2 substituents independently selected from $C_{1-6}$alkyl or $C_{1-6}$alkyloxy$C_{1-6}$alkyl.

Still other particular novel compounds of formula (I-1) are those compounds of formula (I-1) wherein $R^3$ is $Het^1$ or $Ar^1$ wherein $Ar^1$ is naphtyl; or phenyl substituted with 3 substituents each independently selected from halo, $C_{1-6}$alkyl, trifluoromethyl, hydroxy, cyano, $C_{1-6}$alkyloxy, benzyl, benzyloxy, $C_{1-6}$alkylthio, nitro, amino or mono- or di($C_{1-6}$alkyl)amino.

The compounds of the present invention can generally be prepared by reacting an intermediate of formula (VI), wherein Z is bromo or iodo, with an intermediate of formula (VII) under Suzuki coupling conditions. Appropriate Suzuki coupling conditions are for example, stirring a solution of an intermediate (VI) and a tetrakis(triphenylphosphine) palladium catalyst in a reaction-inert solvent, e.g. toluene, in the presence of an appropriate base, e.g. sodium carbonate, while adding intermediate (VII) dissolved in an alcohol, e.g. ethanol.

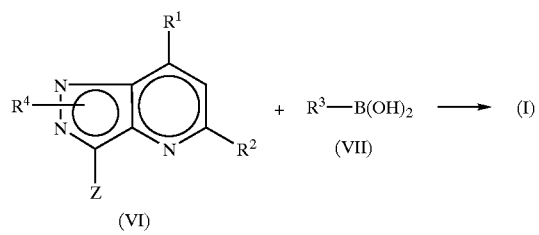

The above-mentioned Suzuki reaction, i.e. a palladium-catalyzed cross-coupling reaction of a phenylboronic acid derivative with a haloarene in the presence of a base, is extensively described in Suzuki A. et al. *Synthetic Communications*, 11:513–519, 1981 and Suzuki A., *Pure and Applied Chemistry*, 66, 213–222 (1994).

Compounds of formula (I-a), defined as compounds of formula (I) wherein $R^1$ has the meaning of $R^1$ other than $C_{1-6}$alkyl, can be prepared by reacting an intermediate of formula (II) with an intermediate of formula (III). In intermediate (II), W is an appropriate leaving group such as halo, e.g. chloro, bromo, or a sulfonyloxy group, e.g. a mesyloxy or a tosyloxy group.

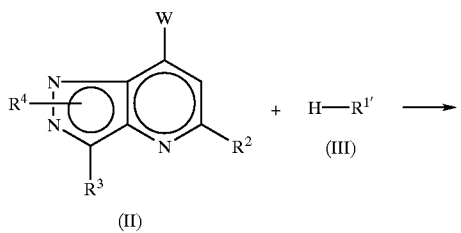

(II)      + H—R$^{1'}$  →

(III)

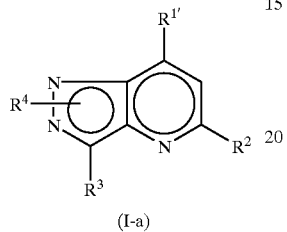

(I-a)

Said reaction can be performed in a reaction-inert solvent such as, for example, acetonitrile, N,N-dimethylformamide, methyl isobutylketone, tetrahydrofuran or dichloromethane; and in the presence of a suitable base such as, for example, sodium carbonate, sodium hydrogen carbonate or triethylamine. When the intermediates of formula (III) are volatile amines, said reaction may also be performed in a sealed reaction vial. Stirring may enhance the rate of the reaction. The reaction may conveniently be carried out at a temperature ranging between room temperature and reflux temperature.

Compounds of formula (I) wherein R$^1$ is OR$^6$, said compounds being represented by formula (I-b), may be prepared by O-alkylating an intermediate of formula (IV) with an intermediate of formula (V), wherein W$^1$ is an appropriate leaving group such as halo, e.g. chloro, bromo, or a sulfonyloxy group, e.g. a mesyloxy or a tosyloxy group.

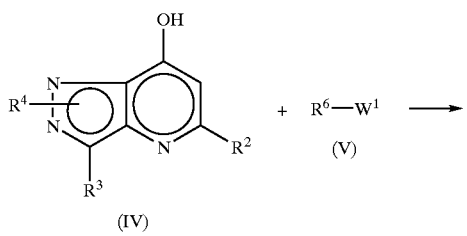

(IV)    + R$^6$—W$^1$  →

(V)

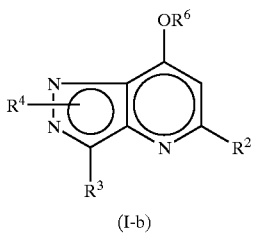

(I-b)

Said reaction for preparing compounds of formula (I-b) can be performed in a reaction-inert solvent such as, for example, N,N-dimethylformamide, and in the presence of a suitable base such as, for example, sodium hydride, preferably at a temperature ranging between room temperature and reflux temperature.

The compounds of formula (I) wherein R$^1$ is —NHR6, represented by formula (I-c), can be prepared by N-alkylating an intermediate of formula (VIII) with an intermediate of formula R$^6$-W, wherein W is as previously defined. Compounds of formula (I-c) can be further N-alkylated with an intermediate of formula R$^5$-W, wherein W is as previously defined, yielding compounds of formula (I-d). These N-alkylations are conducted in a reaction-inert solvent such as, for example, an ether e.g. tetrahydofuran and preferably in the presence of a strong base, e.g. NaH.

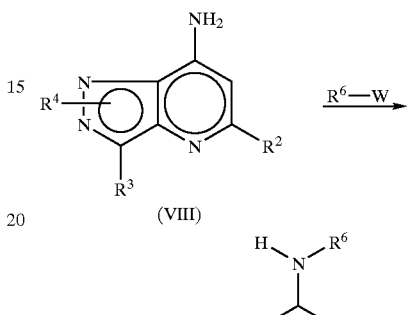

(VIII)     R$^6$—W →

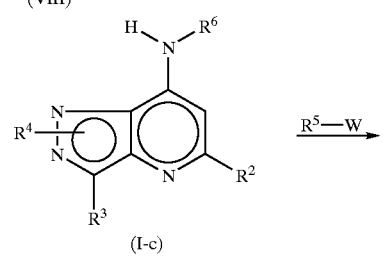

(I-c)     R$^5$—W →

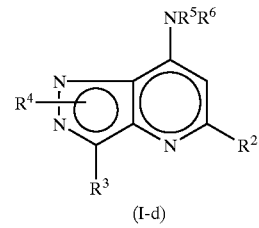

(I-d)

As outlined below, compounds of formula (I) may be converted into each other following art-known transformation procedures.

The compounds of formula (I) may also be converted into each other via art-known reactions or functional group transformations. For instance, compounds of formula (I) bearing a hydroxyC$_{1-6}$alkyl group may be converted into compounds of formula (I) bearing a C$_{1-6}$alkylcarbonyloxyC$_{1-6}$alkyl group, e.g. by treatment with an acid anhydride in an reaction-inert solvent such as, e.g. dichloromethane, and optionally in the presence of a base such as, e.g. pyridine.

The compounds of formula (I) bearing an C$_{1-6}$alkylthio group can be converted into compounds of formula (I) bearing an C$_{1-6}$alkylsulfonyl or C$_{1-6}$alkylsulfoxy group by an oxidation reaction, e.g. treatment with a peroxide such as 3-chloroperbenzoic acid in a reaction-inert solvent, e.g. dichlioromethane. By controlling the amount of oxidant and other reaction parameters, either compounds of formula (I) bearing C$_{1-6}$alkylsulfonyl or C$_{1-6}$alkylsulfoxy can be obtained, or a mixture of both, which subsequently can be separated by conventional methods, e.g. column chromatography.

Compounds of formula (I) bearing a nitro group may be converted to compounds of formula (I) bearing an amino group and subsequently to compounds of formula (I) having a mono- or di(C$_{1-6}$alkyl)amino group. Also, the amino group may be converted using a diazotization reaction to a halo.

Further, the $R^3$ group of compounds of formula (I) can be halogenated using a halogenating agent such as, e.g. chlorine or bromine, in a suitable solvent, e.g. acetic acid, and optionally the reaction may be performed at a temperature ranging between room temperature and the reflux temperature of the reaction mixture.

Furthermore, the compounds of formula (I) may also be prepared as described in EP-0,239,191-A, on pages 6 to 12.

Intermediates of formula (II) can be prepared according to the procedure as described in Robins et al., *J. Heterocyclic Chem.* 22:601–634, 1985.

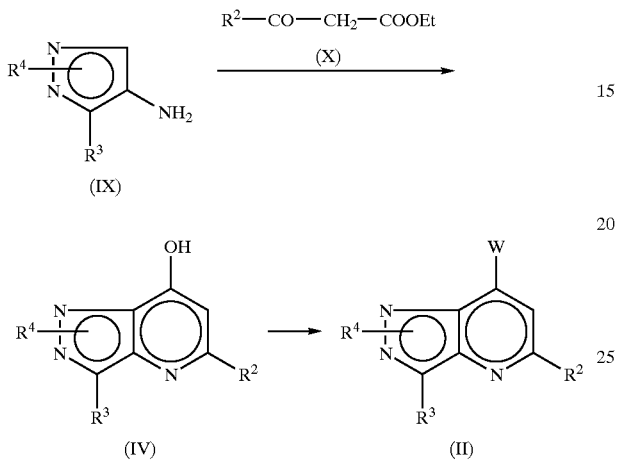

Intermediates of formula (IX) are reacted with a β-keto ester (X), preferably under reflux conditions and in a suitable reaction-inert solvent such as an ether, e.g. THF, yielding intermediates of formula (IX) which are converted into intermediates of formula (II) by converting the hydroxy group of intermediate (VI) into leaving group W, e.g. by treating (IV) with methanesulfonyloxy chloride or a halogenating reagent such as, e.g. POCl$_3$.

Intermediates of formula (VIII) are prepared by treating intermediates of formula (II) with ammonia.

The intermediates of formula (IX) are prepared by reacting an α-phthalimide compound (XI) with dimethylformamide dimethyl acetal under reflux conditions. The intermediate of formula (XII) is subsequently mixed with a hydrazinie, preferably at room temperature and in a suitable solvent such as ethanol.

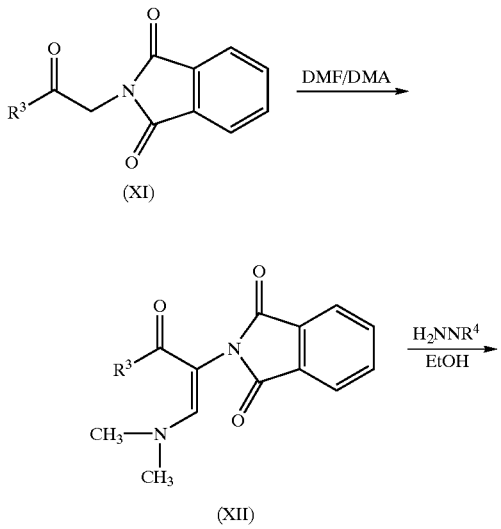

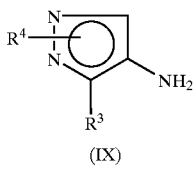

The α-phthalimide intermediate (XI) is generated by reacting a chloroacetyl compound (XIII) with potasium phthalimide in N,N-dimethylformamide.

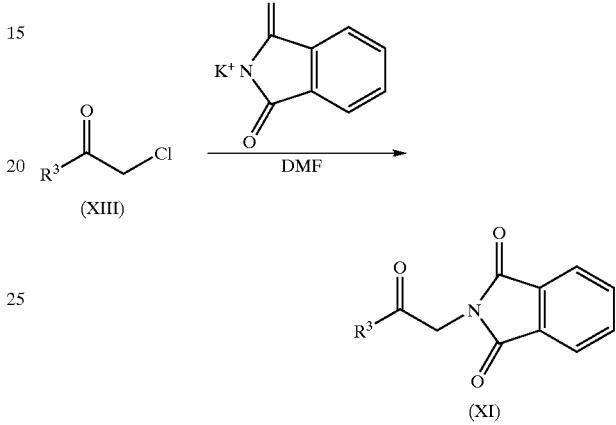

Compounds of formula (I) and some of the intermediates may have one or more stereogenic centers in their structure, present in a R or a S configuration.

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse I*:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g. [$^{125}$I]tyrosine CFR) to receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)). With reference to CRF receptor binding affinities, CRF receptor antagonists of this invention have a $K_i$ of less than 10 $\mu$M. In a preferred embodiment of this invention, a CRF receptor antagonist has a $K_i$ of less than 1 $\mu$M, and more preferably less than 0.25 $\mu$M (i.e., 250 nM).

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, social fobia, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal (including alcoholism). Both prophylactic and therapeutic treatment are envisaged.

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is therapeutically effective to treat a particular disorder, that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorings, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, social fobia, unstable angina, reactive hypertension, anorexia nervosa, bulimia, irritable bowel syndrome, stress-induced immune suppression, stroke, inflammation, Cushing's disease, infantile spasms, epilepsy, substance abuse or withdrawal, and craving.

Hence, this invention provides the use of compounds of formula (I) for the manufacture of a medicine for treating physiological conditions or disorders arising from the hypersecretion of corticotropin-releasing factor (CRF) and in particular for treating the disorders or illnesses mentioned above; and in a further embodiment the use of novel compounds of formula (I) as a medicine is provided. Both prophylactic and therapeutic treatment are envisaged.

EXPERIMENTAL PART

Hereinafter "THF" means tetrahydrofuran and "DCM" means dichloromethane.

A. Preparation of the Intermediates

Example A.1 a) A solution of 2,4-dichloroacetophenone (3.78 g) in THF (20 ml) was cooled to −78° C. under a nitrogen atmosphere. To this stirred solution was added lithium diisopropylamide (LDA) (1.0 M, 22 ml) and the resulting solution was stirred at −78° C. for 15 minutes. Acetoxyacetyl chloride (2.3 ml) was injected and the mixture was stirred for 1 hour and then allowed to warm to room temperature. The reaction was quenched with 1N HCl and the product was extracted with diethyl ether (200 ml). The organic layer was dried, concentrated and recrystallized from ether/hexanes, yielding ethyl 4-(2,4-dichlorophenyl)-2,4-diketobutyrate (intermediate 1).

b) Intermediate (1) (15.4 g) was dissolved in acetic acid and sodium nitrite (3.8 g) in 15 ml water was added slowly. After the exothermic reaction was complete, and the reaction mixture began to cool, methyl hydrazine (6 ml) was added. The reaction mixture was allowed to stir overnight, or until the mixture became yellow. The mixture was concentrated to dryness, giving a yellow oil. This oil was suspended between ether and 2N HCl. The aqueous solution was separated and neutralized with sodium bicarbonate and the slightly basic solution was extracted with ethyl acetate. The ethyl acetate layer was dried and concentrated, yielding 1-methyl-3-carboxyethyl-4-amino-5-(2,4-dichlorophenyl)pyrazole (intermediate 2), which was used without purification in the next step.

c) A solution of intermediate (2) (5 g), ethyl-ethoxy crotonate (2.6 g) and p-toluene-sulfonic acid (100 mg) was stirred and refluxed in xylene (100 ml). After two hours reflux, the reaction mixture was concentrated to a thick oil. This oil was dissolved in 30 ml ethanol and refluxed for 3 hours in the presence of potassium tert-butoxide (2 g). After reflux, the solution was allowed to cool to room temperature and treated with acetic acid (10 ml), then concentrated to dryness. This residue was suspended in ethyl acetate and the resulting solid sodium acetate was filtered off. The filtrate was concentrated to dryness and 5-methyl-6-carboxyethyl-7-hydroxy-2-methyl-4-(2,4'-dichlorophenyl)pyrazolo[4,3-b]pyridine (intermediate 3) was obtained by recrystallisation of the crude filtrate with ethyl ether.

d) A solution of intermediate (3) (1.7 g) and LiOH (1M, 17.5 ml) in ethanol (10 ml) was stirred and heated to reflux and stirred for 16 hours; The solution was then allowed to cool, then poured into HCl (1N, 20 ml). The compound was extracted out with ethyl acetate, dried, and concentrated. The residue was suspended in diphenyl ether (10 ml) and heated for 230° C. for 3 hours. The reaction mixture was allowed to cool, and 5-methyl-7-hydroxy-2-methyl-3-(2,4-dichlorophenyl)pyrazolo[4,3-b]pyridine (intermediate 4) was obtained by purification on a silica column (eluens: ethyl acetate/methanol).

e) Intermediate (4) (400 mg) was suspended in phosphorous oxychloride (2 ml) and refluxed for 2 hours. The reaction mixture was concentrated, yielding 5-methyl-7-chloro-2-methyl-3-(2,4-dichlorophenyl)pyrazolo[4,3-b]pyridine (intermediate 5).

Example A.2 a) To a stirred suspension of potassium phtalimide (92.6 g) in anhydrous DMF (200 ml) at 0° C. was added slowly with stirring trichloroacetophenone (100 g) while keeping the temperature below 5° C. After 1 hour, the reaction mixture was allowed to warm to room temperature. After 16 hours, the solution was concentrated and the resulting residue was partitioned between HCl (1N) and DCM. The combined organic layers were dried, concentrated, and the resulting residue was recrystallized from DCM and diethyl ether, yielding 2-(2-oxo-2-(2,4-dichlorophenylethyl))-1H-indene-1,3(2H)-dione (intermediate 6).

b) Intermediate (6) (50 g) was suspended in dimethyl formamide dimethyl acetal (40 ml). This suspension was heated to 120° C. for 12 hours. The reaction mixture was concentrated and the resulting residue was suspended in diethyl ether and filtered, yielding 1-methyl-4-amino-3-(2,4-dichlorophenyl)pyrazole (intermediate 7).

c) Intermediate (7) (46 g) was suspended in absolute ethanol (200 ml) and stirred under nitrogen. This suspension was heated to 35° C. and one equivalent of methylhydrazine (5.52 g) was added all at once with stirring. This solution was allowed to heat for 10 minutes, followed by a second addition of methyl hydrazine (7 g). The reaction mixture was refluxed for 3 hours, concentrated to a viscous oil, yielding intermediate (8) which was immediately used in the next step without further purification.

d) Crude intermediate (8) was dissolved in benzene (200 ml) and refluxed with a dean-stark trap in the presence of p-toluenesulfonic acid (30 mg). After 1 hour, the reaction mixture was concentrated, and the resulting oil was used in the next step without further purification (intermediate 9).

e) Intermediate (9) was dissolved in diphenyl ether (50 ml) and heated to 250° C. After 30 minutes, the mixture was allowed to cool to room temperature, triturated with hexanes, and concentrated, yielding 5-methyl-7-hydroxy-1-methyl-3-(2,4-dichloro-phenyl)pyrazolo[4,3-b]pyridine (intermediate 10) which was used without further purification.

f) Intermediate (10) was refluxed in the presence of phosphorous oxychloride (45 ml) for 4 hours. The reaction mixture was cooled to room temperature, concentrated and partitioned between ethyl acetate and saturated sodium bicarbonate solution. The aqueous layer was extracted with ethyl acetate. The combined organic layers were dried, concentrated, and the residue was purified over silica gel (eluent: 10% diethyl ether/hexanes), yielding 5-methyl-7-chloro-1-methyl-3-(2,4-dichlorophenyl)-pyrazolo[4,3-b]pyridine (intermediate 11).

B. Preparation of the Final Compounds

Example B.1

Intermediate (5) was suspended in dipropylamine (1 ml) and p-toluenesulfonic acid (30 mg) and heated to 200° C. for 2 hours in a sealed tube. The reaction mixture was cooled and partitioned between ethyl acetate and saturated sodium bicarbonate solution. The organic layer was separated, dried and concentrated. The residue was purified over silica gel (eluens: ethyl acetate/hexanes), yielding 5-methyl-7-(dipropylamino)-2-methyl-3-(2,4-dichlorophenyl)pyrazolo[4,3-b]pyridine (compound 1).

Table F-1 to F-4 list the compounds that were prepared accordingly and table F-5 lists the analytical data for these compounds.

TABLE F-1

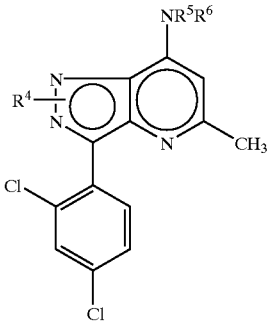

| Co. No. | R⁵ | R⁶ | R⁴ |
|---|---|---|---|
| 4 | —(CH₂)₂CH₃ | —(CH₂)₂CH₃ | 1-CH₃ |
| 5 | —(CH₂)₂OCH₃ | —(CH₂)₂OCH₃ | 1-CH₃ |
| 6 | —(CH₂)₂OCH₃ | —CH₃ | 1-CH₃ |
| 7 | —(CH₂)₂CH₃ | —(CH₂)₂OH | 1-CH₃ |
| 8 | —(CH₂)₂CH₃ | —CH₃ | 1-CH₃ |
| 9 | —(CH₂)₂OCH₃ | —(CH₂)₂CH₃ | 1-CH₃ |
| 10 | H | —CH(CH₂OH)((CH₂)₂CH₃) | 1-CH₃ |
| 11 | —CH₃ | —CH(CH₂OCH₃)((CH₂)₂CH₃) | 1-CH₃ |
| 12 | —(CH₂)₃CH₃ | —(CH₂)₃CH₃ | H |
| 13 | —(CH₂)₃CH₃ | —(CH₂)₃CH₃ | 2-CH₃ |
| 14 | —(CH₂)₃CH₃ | —CH₂CH₃ | 1-CH₃ |
| 15 | —(CH₂)₃CH₃ | —(CH₂)₂CH₃ | 1-CH₃ |
| 16 | —(CH₂)₃CH₃ | —(CH₂)₃CH₃ | 1-CH₂CH₃ |
| 17 | —(CH₂)₃CH₃ | —(CH₂)₃CH₃ | 2-CH₂CH₃ |
| 18 | —(CH₂)₃CH₃ | —(CH₂)₃CH₃ | 1-(CH₂)₂CH₃ |
| 19 | —(CH₂)₃CH₃ | —(CH₂)₃CH₃ | 2-(CH₂)₂CH₃ |
| 20 | —(CH₂)₃CH₃ | —(CH₂)₃CH₃ | 1-CH(CH₃)₂ |
| 21 | —(CH₂)₃CH₃ | (CH₂)₃CH₃ | 2-CH(CH₃)₂ |
| 22 | —(CH₂)₂CH₃ | 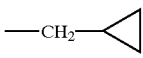 | —H |
| 23 | —(CH₂)₂CH₃ | 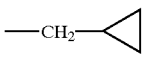 | 1-CH₃ |
| 24 | —(CH₂)₂CH₃ | 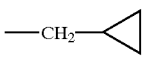 | 2-CH₃ |
| 25 | —(CH₂)₂CH₃ | 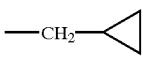 | 1-CH₂CH₃ |
| 26 | —(CH₂)₂CH₃ | 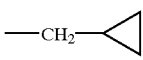 | 2-CH₂CH₃ |
| 27 | —(CH₂)₃CH₃ | —CH₂CH₃ | H |
| 28 | —(CH₂)₃CH₃ | —CH₂CH₃ | 2-CH₃ |
| 29 | —(CH₂)₃CH₃ | —CH₂CH₃ | 1-CH₂CH₃ |
| 30 | —(CH₂)₃CH₃ | —CH₂CH₃ | 2-CH₂CH₃ |
| 31 | —CH₂CH₃ | —(CH₂)₂OCH₃ | 1-CH₃ |
| 31 | —CH₂CH₃ | —(CH₂)₂OCH₃ | 1-CH₃ |
| 32 | —CH(CH₃)₂ | —(CH₂)₂OCH₃ | 1-CH₃ |
| 33 | —H | 4-hydroxyphenylmethyl | 1-CH₃ |
| 34 | —H | —(CH₂)₂OCH₃ | 1-CH₃ |
| 35 | —H | 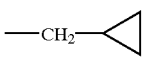 | 1-CH₃ |
| 36 | —(CH₂)₃CH₃ | —(CH₂)₂OCH₃ | 1-CH₃ |
| 37 | —(CH₂)₄CH₃ | —(CH₂)₂OCH₃ | 1-CH₃ |

TABLE F-1-continued

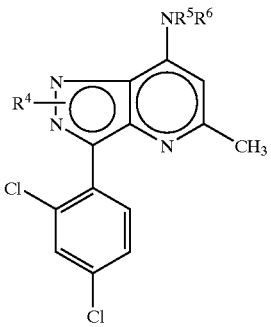

| Co. No. | R⁵ | R⁶ | R⁴ |
|---|---|---|---|
| 38 | —(CH₂)₅CH₃ | —(CH₂)₂OCH₃ | 1-CH₃ |
| 39 | —CH₂CH(CH₃)₂ | —(CH₂)₂OCH₃ | 1-CH₃ |
| 40 | 2-CH₂C(=CH₂)CH₃ | —CH₂CH₃ | 2-CH₃ |
| 41 | —(CH₂)₂CH(CH₃)₂ | —(CH₂)₂CH(CH₃)₂ | 1-CH₃ |
| 42 | —(CH₂)₂N(CH₃)₂ | phenylmethyl | 1-CH₃ |
| 43 | —CH₂CH₃ | 4-methylphenylmethyl | 1-CH₃ |
| 44 | —CH₂CH₃ | 2-fluorophenylmethyl | 1-CH₃ |
| 45 | —CH₂CH₃ | —CH₂—<cyclopropyl> | 1-CH₃ |
| 46 | —(CH₂)₃CH₃ | —CH₂—<cyclopropyl> | 1-CH₃ |
| 47 | —(CH₂)₄CH₃ | —CH₂—<cyclopropyl> | 1-CH₃ |
| 48 | —(CH₂)₅CH₃ | —CH₂—<cyclopropyl> | 1-CH₃ |
| 49 | —CH₂CH(CH₃)₂ | —CH₂—<cyclopropyl> | 1-CH₃ |
| 50 | —(CH₂)₃CH₃ | 4-hydroxyphenylmethyl | 1-CH₃ |
| 51 | —(CH₂)₃CH₃ | phenylmethyl | 1-CH₃ |
| 52 | —(CH₂)₂CH₃ | phenylmethyl | 1-CH₃ |
| 53 | —CH₂CH(CH₃)₂ | —CH₂CH(CH₃)₂ | 1-CH₃ |
| 54 | —CH₂CH₃ | —(CH₂)₃OCH₃ | 1-CH₃ |
| 55 | —(CH₂)₂CH₃ | —(CH₂)₃OCH₃ | 1-CH₃ |
| 56 | —(CH₂)₃CH₃ | —(CH₂)₃OCH₃ | 1-CH₃ |
| 57 | —CH₂CH₃ | —(CH₂)₄CH₃ | 1-CH₃ |
| 58 | —(CH₂)₂CH₃ | —(CH₂)₄CH₃ | 1-CH₃ |
| 59 | —(CH₂)₃CH₃ | —(CH₂)₄CH₃ | 1-CH₃ |
| 60 | —(CH₂)₃CH₃ | 4-methoxyphenylethyl | 1-CH₃ |
| 61 | —(CH₂)₃CH₃ | 2-pyridinylethyl | 1-CH₃ |
| 62 | —(CH₂)₃CH₃ | phenoxyethyl | 1-CH₃ |
| 63 | —(CH₂)₃CH₃ | isopentyl | 1-CH₃ |
| 64 | —CH₂CH₃ | —(CH₂)₂CH₃ | 1-CH₃ |
| 65 | —(CH₂)₃CH₃ | 2-methoxyphenylethyl | 1-CH₃ |
| 66 | —(CH₂)₃CH₃ | 3-methoxyphenylethyl | 1-CH₃ |
| 67 | —(CH₂)₃CH₃ | 4-pyridinylmethyl | 1-CH₃ |
| 68 | —(CH₂)₃CH₃ | 4-pyridinylethyl | 1-CH₃ |
| 69 | —(CH₂)₃CH₃ | 2-furanylmethyl | 1-CH₃ |
| 70 | —(CH₂)₃CH₃ | 2-tetrahydrofuranylmethyl | 1-CH₃ |
| 71 | —(CH₂)₃CH₃ | —(CH₂)₂SCH₃ | 1-CH₃ |
| 72 | —(CH₂)₃CH₃ | —(CH₂)₂OCH(CH₃)₂ | 1-CH₃ |
| 73 | —(CH₂)₃CH₃ | 4-methoxyphenylethyl | 1-CH₃ |

TABLE F-2

Structure: 4-NR⁵R⁶-pyrazolo-pyridine with 2-chloro-4-methylphenyl substituent, R² and R⁴ variable.

| Co. No. | R⁵ | R⁶ | R² | R⁴ |
|---|---|---|---|---|
| 74 | —(CH₂)₃CH₃ | —(CH₂)₃CH₃ | —CH₃ | 1-CH₃ |
| 75 | —(CH₂)₃CH₃ | —(CH₂)₃CH₃ | —CH₃ | 1-CH₃ |
| 76 | —(CH₂)₃CH₃ | —CH₂CH₃ | —CH₃ | 1-CH₃ |
| 77 | —(CH₂)₃CH₃ | —(CH₂)₃CH₃ | —CH₃ | H |
| 78 | —(CH₂)₂CH₃ | —CH₂-cyclopropyl | —CH₃ | H |
| 79 | —(CH₂)₃CH₃ | —(CH₂)₃CH₃ | —CH₃ | 1-CH₂CH₃ |
| 80 | —(CH₂)₃CH₃ | —(CH₂)₃CH₃ | —CH₃ | 2-CH₂CH₃ |
| 81 | —(CH₂)₂CH₃ | —CH₂-cyclopropyl | —CH₃ | 1-CH₂CH₃ |
| 82 | —(CH₂)₂CH₃ | —CH₂-cyclopropyl | —CH₃ | 2-CH₂CH₃ |
| 83 | —(CH₂)₃OCH₃ | —CH₂CH₃ | —CH₃ | 1-CH₃ |
| 84 | —(CH₂)₂CH₃ | —(CH₂)₂CH₃ | —CH₃ | 1-CH₃ |
| 85 | —(CH₂)₂CH₃ | —CH₂CH₃ | —CH₃ | 1-CH₃ |
| 86 | —CH(CH₃)(CH₂CH₃) | —(CH₂)₂CH₃ | —CH₃ | 1-CH₃ |
| 87 | —(CH₂)₂CH₃ | —CH₂-cyclopropyl | —CH₃ | 1-CH₃ |
| 88 | —CH₃ | —(CH₂)₂CH₃ | —CH₃ | 1-CH₃ |
| 89 | —CH₂CH=CH₂ | —CH₂CH=CH₂ | —CH₃ | 1-CH₃ |
| 90 | —(CH₂)₃CH₃ | —CH₃ | —CH₃ | 1-CH₃ |
| 91 | —CH₃ | —(CH₂)₂OCH₃ | —CH₃ | 1-CH₃ |
| 92 | —CH₂CH₃ | —CH₂CH₃ | —CH₃ | 1-CH₃ |

TABLE F-3

Structure: 4-NR⁵R⁶-pyrazolo-pyridine with 2-chloro-4,6-dimethylphenyl substituent.

| Co. No. | R⁵ | R⁶ | R² | R⁴ |
|---|---|---|---|---|
| 93 | —(CH₂)₃CH₃ | —(CH₂)₃CH₃ | —CH₃ | 1-CH₃ |
| 94 | —(CH₂)₃CH₃ | —(CH₂)₃CH₃ | —CH₃ | 2-CH₃ |
| 95 | —(CH₂)₃CH₃ | —CH₂CH₃ | —CH₃ | 1-CH₃ |
| 96 | —CH₂CH₃ | —(CH₂)₃CH₃ | —CH₃ | H |
| 97 | —(CH₂)₃CH₃ | —(CH₂)₃CH₃ | —CH₃ | H |
| 98 | —(CH₂)₃CH₃ | —(CH₂)₃CH₃ | —CH₃ | 2-CH₂CH₃ |
| 99 | —(CH₂)₃CH₃ | —CH₂CH₃ | —CH₃ | 2-CH₂CH₃ |
| 100 | —(CH₂)₃CH₃ | —CH₂CH₃ | —CH₃ | 1-CH₂CH₃ |
| 101 | —(CH₂)₃CH₃ | —(CH₂)₃CH₃ | —CH₃ | 1-CH₂CH₃ |
| 102 | —(CH₂)₃CH₃ | —CH₂-cyclopropyl | —CH₃ | 1-CH₃ |
| 103 | —(CH₂)₂OCH₃ | —(CH₂)₂OCH₃ | —CH₃ | 1-CH₃ |
| 104 | —CH(CH₃)₂ | —CH₂CH₃ | —CH₃ | 1-CH₃ |
| 105 | —CH₃ | phenylmethyl | —CH₃ | 1-CH₃ |

TABLE F-4

Structure: pyrazolo-pyridine with R¹, R³, R⁴ substituents and 6-methyl on pyridine.

| Co. No. | R¹ | R⁴ | R³ |
|---|---|---|---|
| 106 | —N(CH₂CH₂CH₃)₂ | 2-CH₃ | 2-chlorophenyl |
| 107 | —N(CH₂CH₂CH₃)₂ | 2-CH₃ | phenyl |
| 108 | —N(CH₂CH₂CH₃)₂ | 1-CH₃ | 2,4-bis(trifluoromethyl)phenyl |
| 109 | —N(CH₂CH₂CH₂CH₃)₂ | 1-CH₃ | 2,4,6-trimethylphenyl |
| 110 | —N(CH₂CH₂CH₂CH₃)₂ | 2-CH₃ | 2,4,6-trimethylphenyl |
| 111 | 4-methylpiperidin-1-yl | 1-CH₃ | 2-chloro-4,6-dimethylphenyl |
| 112 | —N(CH₂CH₂CH₂CH₃)₂ | H | 2-chloro-4-methoxyphenyl |
| 113 | —N(CH₂CH₂CH₂CH₃)₂ | 1-CH₃ | 2-chloro-4-methoxyphenyl |
| 114 | —N(CH₂CH₂CH₂CH₃)₂ | 2-CH₃ | 2-chloro-4-methoxyphenyl |
| 115 | 2-methylpiperidin-1-yl | 1-CH₃ | 2-chloro-4-methylphenyl |
| 116 | 2-methyl-5-ethyl-piperidin-1-yl | 1-CH₃ | 2,4-dichlorophenyl |
| 117 | —N(CH₂CH₂CH₃)₂ | 1-CH₃ | 4-chlorophenyl |
| 118 | N-thiomorpholinyl | 5-CH₃ | 2,4-dichlorophenyl |
| 119 | (N,N-ethylbutyl)amine | 1-CH₃ | 2-(dimethylamine)-4-methyl-5-pyridinyl |
| 120 | (N,N-butylpentyl)amine | 1-CH₃ | 2,4,6-trimethylphenyl |
| 121 | (N,N-ethylbutyl)amine | 1-CH₃ | 2,4,6-trimethylphenyl |
| 122 | (N,N-methoxyethyl-propyl)amine | 1-CH₃ | 1-naphtyl |
| 123 | (N,N-ethylbutyl)amine | 1-CH₃ | 2-methyl-4-methoxyphenyl |

TABLE F-5

Analytical data

| Co. No. | $^1$H NMR data(CDCl$_3$) |
|---|---|
| 1 | δ0.92(trp, 6H), 1.75(trp, 4H), 2.48(s, 3H), 3.71(m, 2H), 3.82(m, 2H), 4.00(s, 3H), 6.01(s, 1H), 7.51(m, 3H) |
| 2 | δ0.90(trp, 6H), 1.28(m, 4H), 1.53(m, 4H), 2.60(s, 3H), 3.22(trp, 4H), 4.29 (s, 3H), 6.69(s, 1H), 7.37(dd, 1H), 7.56(d, 1H), 7.79(d, 1H) |
| 4 | δ0.89(trp, 6H), 1.58(m, 4H), 2.61(s, 3H), 3.20(trp, 4H), 4.29(s, 3H), 6.69(s, 1H), 7.38(dd, 1H), 7.55(d, 1H), 7.80(d, 1H) |
| 5 | δ2.61(s, 3H), 3.29(s, 6H), 3.52(trp, 8H), 4.31(s, 3H), 6.83(s, 1H), 7.36(dd, 1H), 7.41(d, 1H), 7.78(d, 1H) |
| 6 | δ2.65(s, 3H), 2.97(s, 3H), 3.27(s, 3H), 3.41(m, 4H), 4.35(s, 3H), 6.78(s, 1H), 7.39(dd, 1H), 7.58(d, 1H), 7.81(d, 1H) |
| 7 | δ0.92(trp, 3H), 1.61(m, 2H), 2.59(s, 3H), 3.23(m, 2H), 3.42(trp, 2H), 3.78(m, 2H), 4.30(s, 3H), 6.75(s, 1H), 7.40(dd, 1H), 7.52(d, 1H), 7.76(d, 1H) |
| 8 | δ0.95(trp, 3H), 1.71(m, 2H), 2.59(s, 3H), 2.88(s, 3H), 4.30(s, 3H), 6.67(s, 1H), 7.39(dd, 1H), 7.58(d, 1H), 7.76(d, 1H) |
| 12 | δ0.97(t, 6H), 1.37–1.44(m, 4H), 1.64–1.72(m, 4H), 2.55(s, 3H), 3.62(t, 4H), 6.13(s, 1H), 7.35(dd, 1H), 7.49(d, 1H), 8.22(d, 1H) |
| 13 | δ1.00(t, 6H), 1.39–1.47(m, 4H), 1.64–1.74(m, 4H), 2.54(s, 3H), 3.70–3.80(m, 2H), 3.80–3.92(m, 2H), 3.95(s, 3H), 5.95(s, 1H), 7.42(dd, 1H), 7.48(d, 1H), 7.57(d, 1H) |
| 14 | δ0.88(trp, 3H), 1.05(trp, 3H), 1.41(m, 2H), 1.62(m, 2H), 2.60(s, 3H), 3.30(trp, 2H), 3.32(m, 2H), 4.29(s, 3H), 6.68(s, 1H), 7.39(dd, 1H), 7.52(d, 1H), 7.73(d, 1H) |
| 15 | δ0.93(m, 6H), 1.38(m, 2H), 1.40(m, 2H), 1.60(m, 2H), 2.59(s, 3H), 3.30(m, 4H), 4.30(s, 3H), 6.66(s, 1H), 7.38(dd, 1H), 7.50(d, 1H), 7.79(d, 1H) |
| 16 | δ0.90(t, 6H), 1.26–1.34(m, 4H), 1.41(t, 3H), 1.48–1.54(m, 4H), 2.60(s, 3H), 3.21(t, 4H), 4.61(q, 2H), 6.70(s, 1H), 7.35(dd, 1H), 7.54(d, 1H), 7.80(d, 1H) |
| 17 | δ1.00(t, 6H), 1.37–1.49(m, 4H), 1.67–1.77(m, 4H), 2.49(s, 3H), 3.68–3.77(m, 2H), 3.82–3.92(m, 2H), 4.05–4.15(m, 1H), 4.17–4.28(m, 1H), 5.94(s, 1H), 7.40(dd, 1H), 7.44(d, 1H), 7.56(d, 1H) |
| 18 | δ0.84(t, 3H), 0.90(t, 6H), 1.26–1.34(m, 4H), 1.46–1.56(m, 4H), 1.80–1.90(m, 2H), 2.60(s, 3H), 3.21(t, 4H), 4.53(t, 2H), 6.70(s, 1H), 7.35(dd, 1H), 7.54(d, 1H), 7.77(d, 1H) |
| 19 | δ0.79(t, 3H), 0.99(t, 6H), 1.38–1.47(m, 4H), 1.64–1.76(m, 4H), 1.82–1.90(m, 2H), 2.50(s, 3H), 3.65–3.75(m, 2H), 3.80–3.92(m, 2H), 3.96–4.06(m, 1H), 4.15–4.24(m, 1H), 5.94(s, 1H), 7.39–7.45(m, 2H), 7.57(d, 1H) |
| 20 | δ0.89(t, 6H), 1.26–1.34(m, 4H), 1.46–1.54(m, 10H), 2.60(s, 3H), 3.19(t, 4H), 5.32–5.41(m, 1H), 6.70(s, 1H), 7.35(dd, 1H), 7.54(d, 1H), 7.82(d, 1H) |
| 21 | δ1.00(t, 6H), 1.36(d, 3H), 1.40–1.48(m, 4H), 1.61(d, 3H), 1.68–1.79(m, 4H), 2.50(s, 3H), 3.68–3.92(m, 4H), 4.36–4.45(m, 1H), 5.92(s, 1H), 7.41(d, 2H), 7.57(dd, 1H) |
| 22 | δ0.32–035(m, 2H), 0.59–0.64(m, 2H), 1.00(t, 3H), 1.14–1.22(m, 1H), 1.72–1.80(m, 2H), 2.56(s, 3H), 3.60–3.65(m, 4H), 6.22(s, 1H), 7.40(dd, 1H), 7.52(d, 1H), 8.32(d, 1H) |
| 23 | δ0.06–0.09(m, 2H), 0.47–0.51(m, 2H), 0.93(t, 3H), 1.22–1.24(m, 1H), 1.50–1.62(m, 2H), 2.60(s, 3H), 3.11(d, 2H), 3.32(t, 2H), 4.30(s, 3H), 6.75(s, 1H), 7.35(dd, 1H), 7.54(d, 1H), 7.79(d, 1H) |
| 24 | δ0.34–0.38(m, 2H), 0.57–0.61(m, 2H), 1.00(t, 3H), 1.18–1.24(m, 1H), 1.73–1.81(m, 2H), 2.55(s, 3H), 3.70–3.90(m, 4H), 3.95(s, 3H), 6.05(s, 1H), 7.43(dd, 1H), 7.47(d, 1H), 7.57(d, 1H) |
| 25 | δ0.06–0.08(m, 2H), 0.47–0.51(m, 2H), 0.93(t, 3H), 1.24–1.26(m, 1H), 1.42(t, 3H), 1.50–1.62(m, 2H), 2.61(s, 3H), 3.10(d, 2H), 3.31(d, 2H), 4.64(q, 2H), 6.77(s, 1H), 7.36(dd, 1H), 7.54(d, 1H), 7.80(d, 1H) |
| 26 | δ0.36–0.38(m, 2H), 0.57–0.61(m, 2H), 1.00(t, 3H), 1.18–1.24(m, 1H), 1.45(t, 3H), 1.72–1.85(m, 2H), 2.54(s, 3H), 3.70–3.90(m, 4H), 4.06–4.30(m, 2H), 6.04(s, 1H), 7.42(dd, 1H), 7.45(d, 1H), 7.57(d, 1H) |
| 27 | δ1.00(t, 3H), 1.31(t, 3H), 1.38–1.48(m, 2H), 1.67–1.77(m, 2H), 2.55(s, 3H), 3.63(t, 2H), 3.74(q, 2H), 6.14(s, 1H), 7.40(dd, 1H), 7.52(d, 1H), 8.35(d, 1H) |
| 28 | δ1.00(t, 3H), 1.30(t, 3H), 1.39–1.47(m, 2H), 1.64–1.76(m, 2H), 2.51(s, 3H), 3.70–3.80(m, 2H), 3.80–3.96(m, 2H), 3.95(s, 3H), 5.97(s, 1H), 7.41(dd, 1H); 7.46(d, 1H), 7.57(d, 1H) |
| 29 | δ0.91(t, 3H), 1.09(t, 3H), 1.30–1.38(m, 2H), 1.42(t, 3H), 1.50–1.58(m, 2H), 2.61(s, 3H), 3.19(t, 2H), 3.29(q, 2H), 4.62(q, 2H),6.71(s, 1H), 7.36(dd, 1H), 7.54(d, 1H), 7.79(d, 1H) |
| 30 | δ1.04(t, 3H), 1.34(t, 3H), 1.39–1.47(m, 5H), 1.64–1.78(m, 2H), 2.60(s, 3H), 3.75–4.00(m, 4H), 4.02–4.25(m, 2H), 5.96(s, 1H), 7.45(s, 1H), 7.46(s, 1H), 7.58(s, 1H) |
| 74 | δ0.91(t, 6H), 1.30(m, 4H), 1.35(m, 4H), 2.50(s, 3H), 2.61(s, 3H), 3.23(m, 4H), 4.26(s, 3H), 6.69(s, 1H), 7.32(m, 2H), 7.75(d, 1H) |
| 75 | δ0.90(t, 6H), 1.30(m, 2H), 1.34(m, 4H), 2.49(s, 3H), 2.60(s, 3H), 3.21(m, 2H), 4.27(s, 3H), 6.69(s, 1H), 7.31(m, 2H), 7.75(d, 1H) |
| 76 | δ0.93(t, 3H), 1.09(t, 3H), 1.30(m, 2H), 1.34(m, 2H), 2.47(s, 3H), 2.59(s, 3H), 3.19(t, 2H), 3.29(q, 2H), 4.25(s, 3H), 6.67(s, 1H), 7.30(m, 2H), 7.71(d, 1H) |
| 77 | δ0.97(t, 6H), 1.36–1.46(m, 4H), 1.63–1.73(m, 4H), 2.41(s, 3H), 2.54(s, 3H), 3.54(t, 4H), 6.18(s, 1H), 7.21(dd, 1H), 7.27(d, 1H), 7.62(d, 1H) |
| 78 | δ0.28–0.33(m, 2H), 0.59–0.66(m, 2H), 0.98(t, 3H), 1.08–1.18(m, 1H), 1.70–1.78(m, 2H), 2.44(s, 3H), 2.55(s, 3H), 3.49–3.54(m, 4H), 6.28(s, 1H), 7.25 (dd, 1H), 7.30(d, 1H), 7.69(d, 1H) |
| 79 | δ0.90(t, 6H), 1.23–1.34(m, 4H), 1.41(t, 3H), 1.46–1.57(m, 4H), 2.49(s, 3H), 2.60(s, 3H), 3.20(t, 4H), 4.58(q, 2H), 6.69(s, 1H), 7.26–7.31(m, 2H), 7.78(d, 1H) |
| 80 | δ1.00(t, 6H), 1.38–1.49(m, 4H), 1.67–1.77(m, 4H), 2.17(s, 3H), 2.57(s, 3H), 3.66–3.95(m, 4H), 4.05–4.16(m, 2H), 5.93(s, 1H), 7.22(d, 1H), 7.28(d, 1H), 7.37(s, 1H) |
| 81 | δ0.05–0.08(m, 2H), 0.47–0.51(m, 2H), 0.92(t, 3H), 1.24–1.26(m, 1H), 1.41(t, 3H), 1.50–1.66(m, 2H), 2.48(s, 3H), 2.60(s, 3H), 3.09(d, 2H), 3.32(t, 2H), 4.61(q, 2H), 6.76(s, 1H), 7.26–7.31(m, 2H), 7.77(d, 1H) |
| 82 | δ0.36–0.40(m, 2H), 0.57–0.62(m, 2H), 1.01(t, 3H), 1.18–1.22(m, 1H), 1.41(t, 3H), 1.72–1.85(m, 2H), 2.17(s, 3H), 2.60(s, 3H), 3.70–4.00(m, 4H), 4.06–4.20 (m, 2H), 6.03(s, 1H), 7.22(d, 2H), 7.29(d, 1H), 7.38(s, 1H) |
| 83 | δ1.11(t, 3H), 2.47(s, 3H), 2.60(s, 3H), 3.31(s, 3H), 3.35(m, 2H), 3.43(m, 2H), 3.52(m, 2H), 4.27(s, 3H), 6.74(s, 1H), 7.30(m, 2H), 7.71(d, 1H) |
| 84 | δ0.89(t, 6H), 1.56(m, 4H), 2.48(s, 3H), 2.58(s, 3H), 3.19(t, 4H), 4.25(s, 3H), 6.67(s, 1H), 7.30(m, 2H), 7.71(d, 1H) |
| 85 | δ0.92(t, 3H), 1.09(t, 3H), 1.58(m, 2H), 2.48(s, 3H), 2.59(s, 3H), 3.17(t, 2H), 3.33(q, 2H), 4.27(s, 3H), 6.68(s, 1H), 7.30(m, 2H), 7.72(d, 1H) |
| 86 | δ0.90(q, 6H), 1.17(d, 2H), 1.53(m, 2H), 2.49(s, 3H), 2.61(s, 3H), 3.10(m, 2H), 3.28(m, 1H), 4.27(s, 3H), 6.73(s, 1H), 7.30(m, 2H), 7.72(d, 1H) |
| 87 | δ0.01–0.08(m, 2H), 0.47–0.50(m, 2H), 0.93(t, 3H), 1.55–1.62(m, 3H), 2.48(s, 3H), 2.59(s, 3H), 3.11(d, 2H), 3.33(t, 2H), 4.27(s, 3H), 6.74(s, 1H), 7.26(dd, 1H), 7.30(d, 1H), 7.73(d, 1H) |
| 93 | δ0.91(t, 6H), 1.30(m, 4H), 1.35(m, 4H), 2.51(s, 3H), 2.48(s, 3H), 2.61(s, 3H), 3.23(q, 4H), 4.26(s, 3H), 6.66(s, 1H), 7.20(s, 1H), 7.75(s, 1H) |
| 94 | δ0.90(trp, 3H), 0.97(trp, 3H), 1.24(m, 4H), 1.4(m, 2H), 1.71(m, 2H), 2.07(s, 6H), 2.38(s, 3H), 1.42(s, 3H), 3.81(s, 3H), 3.81(trp, 4H), 5.93(s, 1H), 7.00(s, 2H) |
| 95 | δ0.93(t, 3H), 1.09(t, 3H), 1.30(m, 2H), 1.34(m, 2H), 2.38(s, 3H), 2.47(s, 3H), 2.59(s, 3H), 3.19(t, 2H), 3.29(q, 2H), 4.25(s, 3H), 6.67(s, 1H), 7.18(s, 1H), 7.76(s, 1H) |
| 100 | δ0.93(t, 3H), 1.09(t, 3H), 1.29(t, 3H), 1.30(m, 2H), 1.34(m, 2H), 2.38(s,3H), 2.47(s, 3H), 2.59(s, 3H), 3.19(t, 2H), 3.29(q, 2H), 4.60(q, 2H), 6.70(s, 1H), 7.20(s, 1H), 7.76(s, 1H) |
| 102 | δ0.15(m, 2H), 0.50(m, 2H), 0.92(t, 3H), 1.25(m, 1H), 1.30(m, 2H), 1.49(m, 2H), 2.38(s, 3H), 2.49(s, 3H), 2.60(s, 3H), 3.15(d, 2H), 3.39(t, 2H), 4.30(s, 3H), 6.78(s, 1H), 7.2 (m, 2H), 7.78(s, 1H) |
| 103 | δ2.38(s, 3H), 2.42(s, 3H), 2.60(s, 3H), 3.28(s, 6H), 3.48(s, 8H), 4.35(s, 1H), 6.80(s, 1H), 7.19(s, 1H), 7.76(s, 1H) |

TABLE F-5-continued

Analytical data

| Co. No. | $^1$H NMR data(CDCl$_3$) |
|---|---|
| 106 | δ 0.91(trp, 6H), 1.72(trp, 4H), 2.48(s, 3H), 3.70(m, 2H), 3.80(m, 2H), 3.98(s, 3H), 6.03(s, 1H), 7.39(m, 2H), 7.55(m, 2H) |
| 107 | δ 0.99(trp, 6H), 1.76(trp, 4H), 2.47(s, 3H), 3.75(m, 4H), 4.09(s, 3H), 5.97(s, 1H), 7.35(d, 2H), 7.50(m, 2H), 7.71(d, 1H) |
| 108 | δ 0.87(trp, 6H), 1.56(m, 4H), 2.50(s, 3H), 3.06(m, 4H), 4.40(s, 3H), 6.36(s, 1H), 7.57(d, 1H), 7.71(m, 1H), 8.04(d, 1H) |
| 110 | δ 0.91(trp, 6H), 1.25(m, 4H), 1.52(m, 4H), 2.10(s, 6H), 2.31(s, 3H), 2.54(s, 3H), 3.24(trp, 4H), 4.22(s, 3H), 6.63(s, 1H), 6.93(s, 2H) |

C. Pharmacological Examples

Example C.1

CRF Receptor Binding Activity

Compounds were evaluated for binding activity to the CRF receptor by a standard radioligand binding assay as generally described by DeSouza et al. (*J. Neurosci.* 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay was performed in 1.5 ml Eppendorf tubes using approximately 1×10$^6$ cells per tube stably transfected with human CRF receptors. Each tube received about 0.1 ml of assay buffer (e.g., Dulbecco's phosphate buffered saline, 10 mM magnesium chloride, 20 μM bacitracin) with or without unlabeled sauvagine, urotensin I or CRF (final concentration, 1 μM) to determine nonspecific binding, 0.1 ml of [$^{125}$I] tyrosine—ovine CRF (final concentration approximately 200 pM or approximately the K$_D$ as determined by Scatchard analysis) and 0.1 ml of a membrane suspension of cells containing the CRF receptor. The mixture was incubated for 2 hours at 22° C. followed by the separation of the bound and free radioligand by centrifugation. Following two washes of the pellets, the tubes were cut just above the pellet and monitored in a gamma counter for radioactivity at approximately 80% efficiency. All radioligand binding data was analyzed using a non-linear least-square curve-fitting program.

Binding activity corresponds to the concentration (nM) of the compound necessary to displace 50% of the radiolabeled ligand from the receptor. Compounds 1–32, 36–41, 43–95, 97, 99–104, 106, 107, 109, 110, 112–116, 118–123 were found to have a K$_i$≦250 nM.

What is claimed is:

1. A compound of the formula:

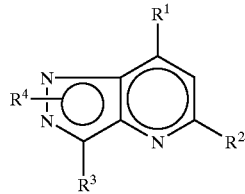

or stereoisomer thereof or the pharmaceutically acceptable acid addition salt form thereof, wherein R$^1$ is C$_{1-6}$alkyl, NR$^5$R$^6$, OR$^6$ or SR$^6$;

R$^2$ is C$_{1-6}$alkyl, C$_{1-6}$alkyloxy, or C$_{1-6}$alkylthio;

R$^3$ is Ar$^1$ or Het$^1$;

R$^4$ is hydrogen or C$_{1-6}$alkyl;

R$^5$ is mono- or di(C$_{3-6}$cycloalkyl)methyl, C$_{3-6}$cycloalkyl, C$_{3-6}$alkenyl, hydroxyC$_{1-6}$alkyl, C$_{1-6}$alkylcarbonyloxy-C$_{1-6}$alkyl, mono- or di(C$_{1-6}$alkyl)aminoC$_{1-6}$alkyl or C$_{1-6}$alkyloxyC$_{1-6}$alkyl;

R$^6$ is mono- or di(C$_{3-6}$cycloalkyl)methyl, Ar$^2$C$_{1-6}$alkyl, Ar$^2$oxy-C$_{1-6}$alkyl, C$_{1-6}$alkyloxyC$_{1-6}$alkyl, hydroxyC$_{1-6}$alkyl, C$_{3-6}$alkenyl, thienylmethyl, furanylmethyl, tetrahydrofuranylmethyl, C$_{1-6}$alkylthioC$_{1-6}$alkyl, mono- or di(C$_{1-6}$alkyl)aminoC$_{1-6}$alkyl, di(C$_{1-6}$alkyl)amino, or C$_{1-6}$alkylcarbonylC$_{1-6}$alkyl;

or R$^5$ and R$^6$ taken together with the nitrogen atom to which they are attached may form a pyrrolidinyl, piperidinyl, or homopiperidinyl, which pyrrolidinyl, piperidinyl, or homopiperidinyl, group is substituted with 1 or 2 substituents each independently selected from the group consisting of C$_{1-6}$alkyl and C$_{1-6}$alkyloxy-C$_{1-6}$alkyl; or R$^5$ and R$^6$ taken together with the nitrogen atom to which they are attached may form a morpholinyl or a thiomorpholinyl group, said morpholinyl or thiomorpholinyl group may optionally be substituted with 1 or 2 substituents independently selected from the group consisting of C$_{1-6}$alkyl and C$_{1-6}$alkyloxyC$_{1-6}$alkyl;

Ar$^1$ is phenyl; naphthyl; or phenyl substituted with 1, 2 or 3 substituents each independently selected from the group consisting of halo, C$_{1-6}$alkyl, trifluoromethyl, hydroxy, cyano, C$_{1-6}$alkyloxy, benzyl, benzyloxy, C$_{1-6}$alkylthio, nitro, amino and mono- or di(C$_{1-6}$alkyl)amino;

Het$^1$ is pyridinyl; pyridinyl substituted with 1, 2 or 3 substituents each independently selected from the group consisting of halo, C$_{1-6}$alkyl, trifluoromethyl, hydroxy, cyano, C$_{1-6}$alkyloxy, benzyloxy, C$_{1-6}$alkylthio, nitro, amino or mono- or di(C$_{1-6}$alkyl)amino; and Ar$^2$ is phenyl; phenyl substituted with 1, 2 or 3 substituents each independently selected from the group consisting of halo, hydroxy, C$_{1-6}$alkyl, C$_{1-6}$alkyloxy, di(C$_{1-6}$alkyl)aminoC$_{1-6}$alkyl, or trifluoromethyl; or pyridinyl.

2. The compound according to claim 1 wherein R$^1$ is a radical of formula NR$^5$R$^6$ wherein R$^5$ is mono- or di(C$_{3-6}$cycloalkyl)methyl, C$_{3-6}$cycloalkyl, C$_{3-6}$alkenyl, hydroxyC$_{1-6}$alkyl, C$_{1-6}$alkylcarbonyloxyC$_{1-6}$alkyl, mono- or di(C$_{1-6}$alkyl)amino-C$_{1-6}$alkyl or C$_{1-6}$alkyloxyC$_{1-6}$alkyl, and R$^6$ is mono- or di(C$_{3-6}$cycloakyl)methyl, Ar$^2$C$_{1-6}$alkyl, Ar$^2$oxyC$_{1-6}$alkyl, hydroxyC$_{1-6}$alkyl, C$_{1-6}$alkyloxy C$_{1-6}$alkyl, C$_{3-6}$alkenyl, thienylmethyl, furanylmethyl, tetrahydrofuranylmethyl, C$_{1-6}$alkylthio C$_{1-6}$alkyl, C$_{1-6}$alkylcarbonylC$_{1-6}$alkyl, mono- or di(C$_{1-6}$alkyl)aminoC$_{1-6}$alkyl, or di(C$_{1-6}$alkyl)amino.

3. The compound according to claim 1 wherein R$^1$ is a radical of formula NR$^5$R$^6$ taken together with the nitrogen atom to which they are attached may form a pyrrolidinyl, piperdinyl, or homopiperidinyl, each substituted with 1 or 2 substituents independently selected from C$_{1-6}$alkyl or C$_{1-6}$alkyloxyC$_{1-6}$alkyl; or R$^5$ and R$^6$ taken together with the nitrogen atom to which they are attached may form a morpholinyl or a thiomorpholinyl group, optionally substituted with 1 or 2 substituents independently selected from C$_{1-6}$alkyl or C$_{1-6}$alkyloxyC$_{1-6}$alkyl.

4. A compound of the formula:

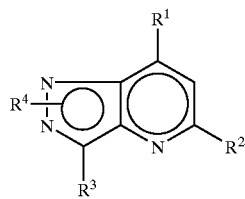

or a stereoisomer thereof or the pharmaceutically acceptable acid addition salt form thereof, wherein $R^1$ is $C_{1-6}$alkyl, $NR^5R^6$, $OR^6$ or $SR^6$;

$R^2$ is $C_{1-6}$alkyl, $C_{1-6}$alkyloxy, or $C_{1-6}$alkylthio;

$R^3$ is $Ar^1$ or $Het^1$;

$R^4$ is hydrogen or $C_{1-6}$alkyl;

$R^5$ is $C_{1-8}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl, mono- or di($C_{1-6}$alkyl)amino$C_{1-6}$alkyl or $C_{1-6}$alkyloxy$C_{1-6}$alkyl;

$R^6$ is $C_{1-8}$alkyl, mono- or di($C_{3-6}$cycloalkyl)methyl, $Ar^2C_{1-6}$alkyl, $Ar^2$oxy$C_{1-6}$alkyl, $C_{1-6}$alkyloxy$C_{1-6}$alkyl, hydroxy$C_{1-6}$alkyl, $C_{3-6}$alkenyl, thienylmethyl, furanylmethyl, tetrahydrofuranylmethyl, $C_{1-6}$alkylthio$C_{1-6}$alkyl, mono- or di($C_{1-6}$alkyl)amino$C_{1-6}$alkyl, di($C_{1-6}$alkyl)amino, or $C_{1-6}$alkylcarbonyl$C_{1-6}$alkyl;

or $R^5$ and $R^6$ taken together with the nitrogen atom to which they are attached may form a pyrrolidinyl, piperidinyl, homopiperidinyl, morpholinyl, or thiomorpholinyl group, optionally substituted with 1 or 2 substituents each independently selected from the group consisting of $C_{1-6}$alkyl and $C_{1-6}$alkyloxy$C_{1-6}$alkyl;

$Ar^1$ is naphthyl; or phenyl substituted with 1, 2 or 3 substituents each independently selected from the group consisting of halo, $C_{1-6}$alkyl, trifluoromethyl, hydroxy, cyano, $C_{1-6}$alkyloxy, benzyl, benzyloxy, $C_{1-6}$alkylthio, nitro, amino and mono- or di($C_{1-6}$alkyl)amino;

$Het^1$ is pyridinyl; pyridinyl substituted with 1, 2 or 3 substituents each independently selected from the group consisting of halo, $C_{1-6}$alkyl, trifluoromethyl, hydroxy, cyano, $C_{1-6}$alkyloxy, benzyloxy, $C_{1-6}$alkylthio, nitro, amino and mono- or di($C_{1-6}$alkyl)amino; and $Ar^2$ is phenyl; phenyl substituted with 1, 2 or 3 substituents each independently selected from the group consisting of halo, hydroxy, $C_{1-6}$alkyl, $C_{1-6}$alkyloxy, di($C_{1-6}$alkyl)amino$C_{1-6}$alkyl, and trifluoromethyl; or pyridinyl.

5. A compound of the formula:

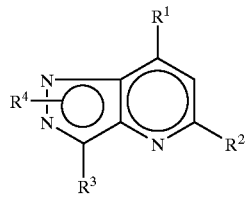

or stereoisomer thereof or the pharmaceutically acceptable acid addition salt form thereof, wherein $R^1$ is $C_{1-6}$alkyl, $NR^5R^6$, $OR^6$ or $SR^6$;

$R^2$ is $C_{1-6}$alkyl, $C_{1-6}$alkyloxy, or $C_{1-6}$alkylthio;

$R^3$ is is $Ar^1$ or $Het^1$;

$R^4$ is $C_{1-6}$alkyl;

$R^5$ is hydrogen, $C_{1-8}$alkyl, mono- or di($C_{3-6}$cycloalkyl)methyl, $C_{1-6}$cycloalkyl, $C_{3-6}$alkenyl, hydroxy$C_{1-6}$alkyl, $C_{1-6}$alkylcarbonyloxy$C_{1-6}$alkyl, mono- or di($C_{1-6}$alkyl)amino$C_{1-6}$alkyl or $C_{1-6}$alkyloxy$C_{1-6}$alkyl;

$R^6$ is $C_{1-8}$alkyl, mono- or di($C_{3-6}$cycloalkyl)methyl, $Ar^2C_{1-6}$alkyl, $Ar^2$oxy$C_{1-6}$alkyl, $C_{1-6}$alkyloxy$C_{1-6}$alkyl, hydroxy$C_{1-6}$alkyl, $C_{3-6}$alkenyl, thienylmethyl, furanylmethyl, tetrahydrofuranylmethyl, $C_{1-6}$alkylthio$C_{1-6}$alkyl, mono- or di($C_{1-6}$alkyl)amino$C_{1-6}$alkyl, di($C_{1-6}$alkyl)amino, or $C_{1-6}$alkylcarbonyl$C_{1-6}$alkyl;

or $R^5$ and $R^6$ taken together with the nitrogen atom to which they are attached may form a pyrrolidinyl, piperidinyl, homopiperidinyl, morpholinyl, or thiomorpholinyl group optionally substituted with 1 or 2 substituents each independently selected from the group consisting of $C_{1-6}$alkyl and $C_{1-6}$alkyloxy-$C_{1-6}$alkyl;

$Ar^1$ is phenyl; naphthyl; or phenyl substituted with 1, 2 or 3 substituents each independently selected from the group consisting of halo, $C_{1-6}$alkyl, trifluoromethyl, hydroxy, cyano, $C_{1-6}$alkyloxy, benzyl, benzyloxy, $C_{1-6}$alkylthio, nitro, amino and mono- or di($C_{1-6}$alkyl)amino;

$Het^1$ is pyridinyl; pyridinyl substituted with 1, 2 or 3 substituents each independently selected from the group consisting of halo, $C_{1-6}$alkyl, trifluoromethyl, hydroxy, cyano, $C_{1-6}$alkyloxy, benzyloxy, $C_{1-6}$alkylthio, nitro, amino and mono- or di($C_{1-6}$alkyl)amino; and $Ar^2$ is phenyl; phenyl substituted with 1, 2 or 3 substituents each independently selected from the group consisting of halo, hydroxy, $C_{1-6}$alkyl, $C_{1-6}$alkyloxy, di($C_{1-6}$alkyl)amino$C_{1-6}$alkyl, and trifluoromethyl; or pyridinyl.

6. A pharmaceutical composition comprising a therapeutically effective amount of a compound according to claim 1 and a pharmaceutically acceptable carrier therefore.

7. A pharmaceutical composition comprising a therapeutically effective amount of a compound according to claim 4 and a pharmaceutically acceptable carrier therefore.

8. A pharmaceutical composition comprising a therapeutically effective amount of a compound according to claim 5 and a pharmaceutically acceptable carrier therefor.

9. A method of treating a patient suffering from a physiological condition or disorder selected from the group consisting of neuropsychiatric disorder, Cushing's disease, infantile spasms, seizures and substance abuse and withdrawal comprising administering to said patient a corticotropin releasing factor antagonistic effective amount of a compound of the formula:

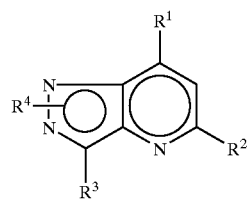

or stereoisomer thereof or the pharmaceutically acceptable acid addition salt form thereof, wherein R¹ is $C_{1-6}$alkyl, $NR^5R^6$, $OR^6$, or $SR^6$;

R² is $C_{1-6}$alkyl, $C_{1-6}$alkoxy, or $C_{1-6}$alkylthio;

R³ is $Ar^1$ or $Het^1$;

R⁴ is hydrogen or $C_{1-6}$alkyl;

R⁵ is hydrogen, $C_{1-8}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl, mono- or di($C_{1-6}$alkyl)amino$C_{1-6}$alkyl or $C_{1-6}$alkyloxy$C_{1-6}$alkyl;

R⁶ is $C^{1-8}$alkyl, mono- or di($C_{3-6}$cycloalkyl)methyl, $Ar^2C_{1-6}$alkyl, $Ar^2$oxy$C_{1-6}$alkyl, $C_{1-6}$alkyloxy$C_{1-6}$alkyl, hydroxy$C_{1-6}$alkyl, $C_{3-6}$alkenyl, thienylmethyl, furanylmethyl, tetrahydrofuranylmethyl, $C_{1-6}$alkylthio$C_{1-6}$alkyl, mono- or di($C_{1-6}$alkyl)amino$C_{1-6}$alkyl, di($C_{1-6}$alkyl)amino, or $C_{1-6}$alkylcarbonyl$C_{1-6}$alkyl;

or R⁵ and R⁶ taken together with the nitrogen atom to which they are attached may form a pyrrolidinyl, piperidinyl, homopiperidinyl, morpholinyl, or thiomorpholinyl group optionally substituted with 1 or 2 substituents each independently selected from $C_{1-6}$alkyl or $C_{1-6}$alkyloxy$C_{1-6}$alkyl;

$Ar^1$ is phenyl; naphthyl; or phenyl substituted with 1, 2 or 3 substituents each independently selected from the group consisting of halo, $C_{1-6}$alkyl, trifluoromethyl, hydroxy, cyano, $C_{1-6}$alkyloxy, benzyl, benzyloxy, $C_{1-6}$alkylthio, nitro, amino and mono- or di($C_{1-6}$alkyl)amino;

$Het^1$ is pyridinyl; pyridinyl substituted with 1, 2 or 3 substituents each independently selected from the group consisting of halo, $C_{1-6}$alkyl, trifluoromethyl, hydroxy, cyano, $C_{1-6}$alkyloxy, benzyloxy, $C_{1-6}$alkylthio, nitro, amino and mono-or di($C_{1-6}$alkyl)amino; and $Ar^2$ is phenyl; phenyl substituted with 1, 2 or 3 substituents each independently selected from the group consisting of halo, hydroxy, $C_{1-6}$alkyl, $C_{1-6}$alkyloxy, di($C_{1-6}$alkyl)amino$C_{1-6}$alkyl, and trifluoromethyl; or pyridinyl.

10. The method according to claim 9 wherein R¹ is $NR^5R^6$ wherein R⁵ is hydrogen or $C_{1-8}$alkyl; and R⁶ is $C_{1-8}$alkyl or $C_{3-6}$cycloalkylmethyl; or R¹ is $OR^6$ or $SR^6$ wherein R⁶ is $C_{1-6}$alkyl; R² is $C_{1-6}$alkyl; R³ is a phenyl substituted with 1, 2 or 3 substituents each independently selected from $C_{1-6}$alkyl, $C_{1-6}$alkyloxy or halo; or R³ is a pyridinyl substituted with 1, 2 or 3 substituents each independently selected from halo, amino, nitro, trifluoromethyl, mono- or di($C_{1-6}$alkyl)amino, or $C_{1-6}$alkyl; and R⁴ is hydrogen or $C_{1-6}$alkyl.

11. The method according to claim 9 wherein the disorder is a neuropsychiatric disorder.

12. The method according to claim 9 wherein the physiological condition is Cushing's disease, infantile spasms, seizures, or substance abuse and withdrawal.

13. The method according to claim 12 wherein the physiological condition is epilepsy.

14. A method of treating an endocrine, psychiatric or neurologic disorder or illness suffered by a patient comprising administering to said patient an effective amount of a compound to treat said disorder or illness having the formula:

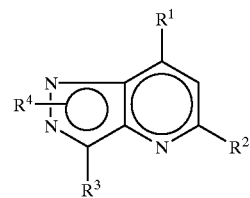

or stereoisomer thereof or the pharmaceutically acceptable acid addition salt form thereof, wherein R¹ is $C_{1-6}$alkyl, $NR^5R^6$, $OR^6$, or $SR^6$;

R² is $C_{1-6}$alkyl, $C_{1-6}$alkoxy, or $C_{1-6}$alkylthio;

R³ is $Ar^1$ or $Het^1$;

R⁴ is hydrogen or $C_{1-6}$alkyl;

R⁵ is hydrogen, $C_{1-8}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl, mono- or di($C_{1-6}$alkyl)amino$C_{1-6}$alkyl or $C_{1-6}$alkyloxy$C_{1-6}$alkyl;

R⁶ is $C_{1-8}$alkyl, mono- or di($C_{3-6}$cycloalkyl)methyl, $Ar^2C_{1-6}$alkyl, $Ar^2$oxy$C_{1-6}$alkyl, $C_{1-6}$alkyloxy$C_{1-6}$alkyl, hydroxy$C_{1-6}$alkyl, $C_{3-6}$alkenyl, thienylmethyl, furanylmethyl, tetrahydrofuranylmethyl, $C_{1-6}$alkylthio$C_{1-6}$alkyl, mono- or di($C_{1-6}$alkyl)amino$C_{1-6}$alkyl, di($C_{1-6}$alkyl)amino, or $C_{1-6}$alkylcarbonyl$C_{1-6}$alkyl;

or R⁵ and R⁶ taken together with the nitrogen atom to which they are attached may form a pyrrolidinyl, piperidinyl, homopiperidinyl, morpholinyl, or thiomorpholinyl group optionally substituted with 1 or 2 substituents each independently selected from $C_{1-6}$alkyl or $C_{1-6}$alkyloxy$C_{1-6}$alkyl;

$Ar^1$ is phenyl; naphthyl; or phenyl substituted with 1, 2 or 3 substituents each independently selected from the group consisting of halo, $C_{1-6}$alkyl, trifluoromethyl, hydroxy, cyano, $C_{1-6}$alkyloxy, benzyl, benzyloxy, $C_{1-6}$alkylthio, nitro, amino and mono- or di($C_{1-6}$alkyl)amino;

$Het^1$ is pyridinyl; pyridinyl substituted with 1, 2 or 3 substituents each independently selected from the group consisting of halo, $C_{1-6}$alkyl, trifluoromethyl, hydroxy, cyano, $C_{1-6}$alkyloxy, benzyloxy, $C_{1-6}$alkylthio, nitro, amino and mono- or di($C_{1-6}$alkyl)amino; and $Ar^2$ is phenyl; phenyl substituted with 1, 2 or 3 substituents each independently selected from the group consisting of halo, hydroxy, $C_{1-6}$alkyl, $C_{1-6}$alkyloxy, di($C_{1-6}$alkyl)amino$C_{1-6}$alkyl, and trifluoromethyl; or pyridinyl.

15. The method according to claim 14 wherein R¹ is $NR^5R^6$ wherein R⁵ is hydrogen or $C_{1-8}$alkyl; and R⁶ is $C_{1-8}$alkyl or $C_{3-6}$cycloalkylmethyl; or R¹ is $OR^6$ or $SR^6$ wherein R⁶ is $C_{1-6}$alkyl; R² is $C_{1-6}$alkyl, R³ is a phenyl substituted with 1,2 or 3 substituents each independently selected from $C_{1-6}$alkyl, $C_{1-6}$alkyloxy or halo; or R³ is a pyridinyl substituted with 1, 2 or 3 substituents each independently selected from halo, amino, nitro, trifluoromethyl, mono- or di($C_{1-6}$alkyl)amino, or $C_{1-6}$alkyl; and R⁴ is hydrogen or $C_{1-6}$alkyl.

* * * * *